United States Patent [19]

Metzger

[11] Patent Number: 4,994,048
[45] Date of Patent: Feb. 19, 1991

[54] APPARATUS AND METHOD FOR CONNECTING A PASSAGEWAY AND OPENINGS WITH A CONNECTOR

[75] Inventor: Mark G. Metzger, Sandy, Utah

[73] Assignee: Becton, Dickinson and Company, Franklin Lakes, N.J.

[21] Appl. No.: 246,476

[22] Filed: Sep. 19, 1988

[51] Int. Cl.⁵ ............................................. A61M 25/00
[52] U.S. Cl. ..................................... 604/283; 604/905
[58] Field of Search .................. 604/283, 905, 27; 285/353, 354, 384, 386, 131, 137.1; 128/672, 673, 675; 219/132, 137.9, 137.63; 901/42

[56] References Cited

U.S. PATENT DOCUMENTS

| | | | |
|---|---|---|---|
| 3,196,375 | 7/1965 | Jones | 128/675 X |
| 3,345,086 | 10/1967 | Wallace | 285/354 X |
| 3,751,077 | 8/1973 | Hiszpanski | 285/386 X |
| 3,805,794 | 4/1974 | Schlesinger | 604/283 |
| 4,417,890 | 11/1983 | Dennehey et al. | 604/905 X |
| 4,508,103 | 4/1985 | Calisi . | |
| 4,517,844 | 5/1985 | Powell | 128/672 X |
| 4,541,537 | 9/1985 | Sailor | 285/353 |
| 4,557,261 | 12/1985 | Rugheimer | 604/283 X |
| 4,608,482 | 8/1986 | Cox et al. | 219/132 |
| 4,629,455 | 12/1986 | Kanno | 604/283 X |
| 4,673,400 | 6/1987 | Martin | 604/283 |
| 4,718,425 | 1/1988 | Tanaka et al. | 128/673 |
| 4,777,951 | 10/1988 | Cribier et al. | 128/672 |
| 4,779,625 | 10/1988 | Cole | 128/673 |
| 4,805,630 | 2/1989 | Storey | 128/675 |
| 4,976,615 | 1/1989 | Bullock et al. | 604/283 X |

*Primary Examiner*—Robert Bahr
*Assistant Examiner*—Jennifer L. Doyle
*Attorney, Agent, or Firm*—Aaron Passman

[57] ABSTRACT

A connector body with a first end and a first part thereon and a second end and a first part thereon includes a passageway aligned along an axis passing through the first end and part. Openings in second part permit communication from the first end to the second end since the openings extend from the second end to at least the passageway. A male luer taper located on the first part about the passageway tapers outwardly of the axis from the first end to a annular groove. A luer nut with an internally threaded collar and an apertured flanged portion seats within the groove permitting rotary but not axial movement of the luer nut relative to the taper. A method provides a plurality of connections between openings and a passageway with a connector body having a first end and a first part thereon and a second end and a second part thereon and a passageway through the first part from the first end extends to a plurality of openings in the second part permitting communication. The method includes locating a male luer taper on the body. A groove near the taper may be included for an internally threaded luer nut.

34 Claims, 2 Drawing Sheets

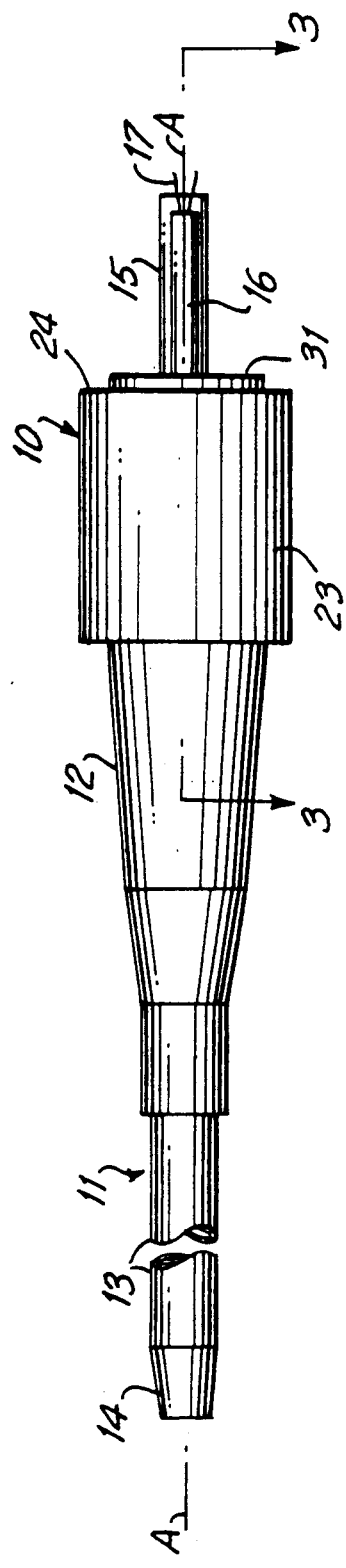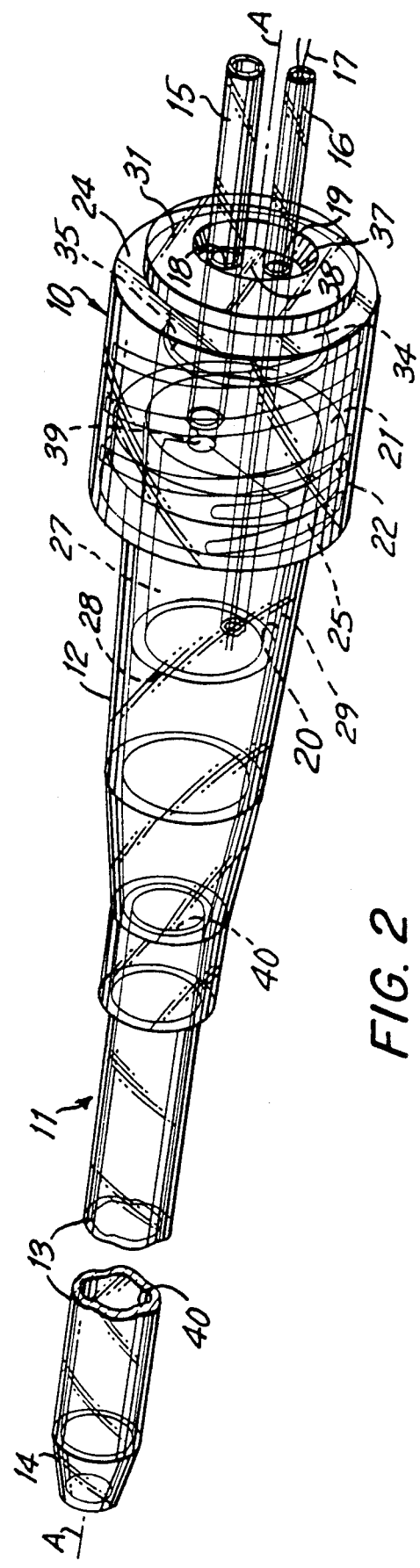

4,994,048

APPARATUS AND METHOD FOR CONNECTING A PASSAGEWAY AND OPENINGS WITH A CONNECTOR

BACKGROUND OF THE INVENTION

1. Field of the Invention.

This invention relates to an apparatus and method for connecting a plurality of openings in a connector to a catheter adapter, and more specifically, to an apparatus and method for the passage through the connector of blood samples, electric circuitry and the like between the openings and a catheter.

2. Background Description.

Connectors which provide multiple ports for entry into a catheter lumen are disclosed in U.S. Pat. Nos. 3,766,916 and 4,096,860. In these patents Y-shaped fittings designed for placement between a catheter adapter and two infusion or sampling sets are shown. In U.S. Pat. No. 3,766,916 the Y-shaped fitting has a tapered front portion to mate with a sleeve connected to the catheter tube. The sleeve and taper are bonded with epoxy and no other provision for securing them is disclosed. One leg of the Y-shaped fitting is in-line with the lumen of the catheter and the other joins the fitting body at angle to the straight flow path through the fitting. There are no threaded members on the fitting to lock the connections with the catheter or the infusion or sampling systems.

The fitting shown in U.S. Pat. No. 4,096,860 is also Y-shaped and includes a threaded connection so that the leading end of the fitting may be screwed into the catheter hub to form a locking luer connection. The problem with Y-shaped fittings of the type described is that the angularly extending leg tends to create difficulties in use. In particular, the fitting and catheter hub or adapter have to be taped or secured to the patient and the bulk of the Y-shaped fitting causes discomfort as well as the possibility of torque applications by way of the extended leg. The force transmitted through the angled leg upon movement of the patient whether intentional or inadvertent may dislodge or unscrew one or more of the connections. Accidental disconnections are dangerous to the patient since the proper medication of the patient requires secure and liquid tight connections. Secure and fluid tight connections prevent blood and fluid lose. A compact multiple port connector is lacking in the teachings of the described Y-shaped fittings.

One approach to providing a locking male luer taper is shown in U.S. Pat. No. 4,266,815 where a tubing connector has a luer nut for locking a male taper. The connector therein locates the luer nut on a square part of the connector whereby the entire connector must be twisted to make the threaded connection. The connector disclosed joins tubing through a female locking luer fitting when the luer nut axially pulls the male and female luer tapers together. The luer nut bears against a shoulder on the connector to apply the locking axial load as the fitting is threaded onto the female luer. The difficultly in using this arrangement is that the luer nut is not captured relative to the fitting so as to allow rotary movement for threading while axially joining and locking the tapers. Only one lumen is provided with this threaded locking luer connector. The problems, difficulties and complications of the described fittings are such that a compact locking connector with multiple inlet ports for a catheter lumen is needed but has been unavailable. The method of making such a connection has also been unknown.

SUMMARY OF THE INVENTION

In the preferred form of the invention a connector comprises a body with a first end and a second end and a first part on the first end and a second part on the second end. A passageway aligned along an axis of the body passes through the first part from the first end into the body. A plurality of openings in second part and parallel to the axis permit communication through the body from the first end to the second end because each of the openings extends from the second end to at least the passageway in the body In a preferred embodiment a combination of at least one of the openings and a portion of the passageway provide a tube lumen generally parallel to the axis of the passageway in the first end. Another aspect of the present invention may include a connector body wherein the first and second ends are parallel to each other and normal to the axis.

In one form of the invention a recess is part of the second end and extends into the second part and has a bottom from which the openings pass through the second part to the passageway. A male luer taper is located on the first part of the body about the passageway and tapers outwardly of the axis from the first end to an enlarged diameter providing a place to connect an adapter. An annular groove circumscribes the body immediately adjacent to the enlarged diameter of male luer taper.

In a preferred embodiment of the invention a luer nut with an internally threaded collar and an apertured flanged end seats within the annular groove and the collar extends over the male luer taper. The fit between the groove and flanged portion permits rotary but not axial movement of the luer nut relative to the taper so as to provide a threaded locking luer.

In a preferred application of the connector the lumen defined by the combination of one of the openings and a portion of the passageway may contain a part of an electrical circuit connecting a catheter transducer to a circuit for transmitting and receiving electrical excitations and signals, respectively. The transducer may be a pressure probe.

The connector of the present invention may include at least a venting and electrical circuit and a tube each in one of the of openings. There is a substantially parallel spaced a part relation between the tube, the electrical circuit and the axis of the connector. The tube extends from the passageway through the second part and beyond the second end.

In an alternate form a coupling in the form of a tubular inlet extends outwardly of the second end from the bottom of the recess for providing a place to receive a cable sheath for the wires of an electric circuit. The coupling and the openings are substantially parallel to one another and the axis of the body.

The present invention also includes a method for providing a plurality of connections between openings and a passageway. A connector having a body with a first end and a second end and a first part on the first end and a second part on the second end is provided with a passageway through the first part from the first end into the body. A plurality of openings in the second part are extended to at least the passageway to permit communication through the body from the first end to the second end and the passageway and at least one of the openings are essentially parallel to an axis of the body.

The method step of locating a male luer taper on the body first part about the passageway so that the male luer tapers outwardly of the axis from the first end to an enlarged diameter with a place immediately adjacent to the enlarged diameter to secure an adapter. An annular groove is situated about the body to connect the adapter. The method may include the added step of placing an internally threaded luer nut with a collar extending over the male luer taper and an apertured flanged portion shaped to seat within the annular groove thereby permitting rotary but not axial movement of the luer nut relative to the taper so as to provide a threaded locking luer.

BRIEF DESCRIPTION OF THE DRAWINGS

FIG. 1 side elevational view of a preferred embodiment of a connector for providing communication between a passageway into a catheter lumen and openings for infusion, sampling or circuitry.

FIG. 2 is a perspective view of the preferred embodiment of a connector shown from an angle which discloses the tubes extending from the openings for infusion, sampling, venting or circuitry.

DETAILED DESCRIPTION OF THE DRAWING

Figure 3:
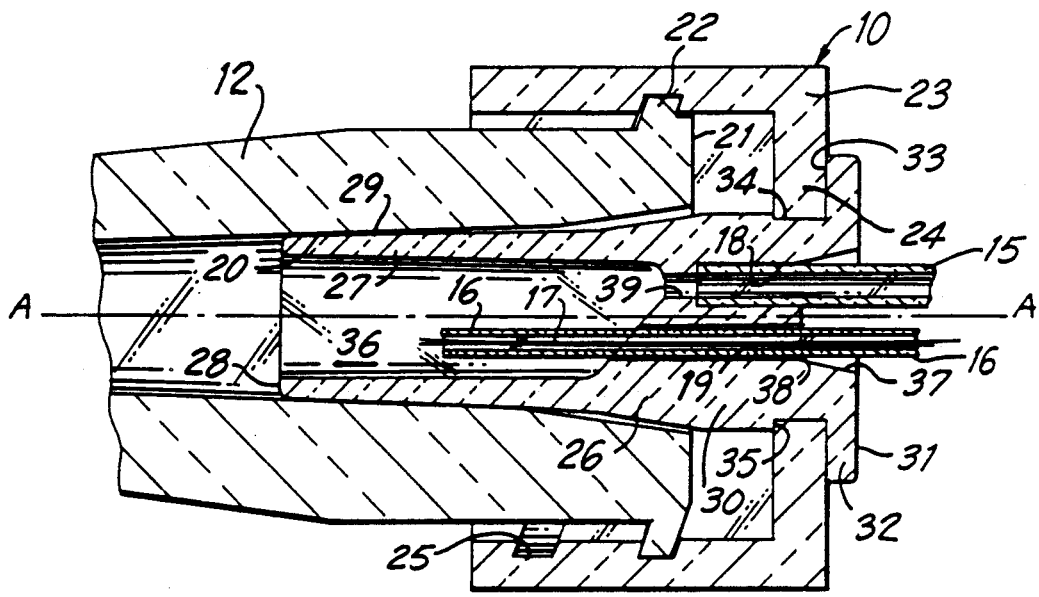
FIG. 3 is an enlarged cross sectional view, taken along line 3—3 of FIG. 1, of the connector of the present invention with tubing and circuitry passing through the openings from outside the connector to a catheter adapter locked onto the tapered part of the connector.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

FIG. 1 is the side elevational view illustrating the overall appearance of the preferred embodiment of a connector 10 used in combination with a catheter assembly 11. The catheter assembly 11 includes a catheter or other type of adapter 12 and a catheter 13. The catheter 13 is a thin flexible polymeric thin wall tube extruded from material such as polyurethane. A tapered tip 14 is used on the catheter tube 13 to ease insertion with an introducer technique. The catheter 13 is connected for communication with the adapter 12. Extending from the connector 10 in the direction opposite of the catheter adapter 12 are a pair of tubes 15 and 16. Tube 15 is for taking samples or administering an infusate. Tube 16 is for providing an atmosphere reference and for carrying an electrical circuit to a probe (not shown) disposed within the catheter 13. Representative of a portion of the electrical circuit, wires or other conductors 17 extend through probe tube 16. The catheter assembly 11 and the connector 10 are preferably symmetrical about the plane of the paper on which FIG. 1 is shown.

FIG. 2 is a perspective view of the preferred embodiment of the connector 10 shown from an angle which discloses the tubes 15 and 16 and how they enter openings 18 and 19 respectively, in connector 10. Although not required, the parts of the connector 10 are preferably molded of a transparent plastic material such as polyvinyl chloride, acrylic or polycarbonate. The perspective illustration of FIG. 2 shows the conjugate cooperative relationship between the catheter adapter 12 and the connector 10. More specifically, the catheter adapter 12 includes on the inside thereof a female luer taper 20 and a radially outward extending flanged end 21 having a luer thread 22 as shown in FIG. 3.

A luer nut 23, shown in FIGS. 2 and 3, extends over the threaded end of catheter adapter 12. In particular, luer nut 23 includes an apertured flange end wall 24 the aperture of which is generally coaxial with axis A. Luer nut 23 also includes an internal or female luer thread 25. The thread 25 is shaped and positioned to cooperate with luer thread 22 on catheter adapter 12. The apertured flange end wall 24 is of an axial thickness sufficient to provide a bearing-like area of adequate strength and size to permit the luer nut 23 to be supported for rotary but not axial motion relative to the catheter adapter 12.

The connector body 26 in FIG. 3 has a first part 27 extending from a first end 28 with a male luer taper 29 located for cooperative interengagement to conjugate with the female luer taper 20 on catheter adapter 12. That is to say that luer tapers 20 and 29 are such that a fluid tight junction is obtained upon axial movement of one into the other. Connector body 26 also includes a second part 30 extending from a second end 31 having an annular flange 32 with a radial wall 33 against which the luer nut 23 bears during unthreading of the luer nut in the nature of an axial thrust bearing relationship. Normal to radial wall 33 and upon connector body 26 is a annular groove 34 which circumscribes the connector body 26 in the area of the second part 30 immediately adjacent to radial wall 33. The annular groove 34 forms a bearing surface for the apertured flange end wall 24 of luer nut 23. Axially along connector body 26 toward male luer taper 29 but defining the annular groove 34 is a shoulder 35 which is the part of the annular groove 34 designed to take the axial thrust of the luer nut 23 as it is threaded onto the catheter adapter 12. The thrust is thereby exerted upon the male luer taper 29 to seat and lock the male luer taper 29 to the female luer taper 20 of the adapter 12.

Within connector body 26 there is a passageway 36 positioned along axis A and immediately beneath the first part 27 of the connector body 26 which includes the male luer taper 29. Passageway 36 is in the form of a hollow cavity or bore which extends axially from the first end into the connector body 26 to beyond the point where the male luer taper 29 ends. As part of the second end and extending into the second part 30 of connector body 26 from the annular flange 32 is a recess 37 in the form of chamfered hole with a bottom 38 through which openings 18 and 19 pass.

Opening 18 has a substantially uniform diameter until a reduced section 39 is reached. Reduced section 39 connects the uniform part of opening 18 with passageway 36. Opening 19 has a substantially uniform diameter throughout and extends from the bottom 38 of the recess 37 to the passageway 36. As shown in FIG. 3 opening 18 has a tube 15 which seats against the reduced section 39. Opening 19 has a tube 16 which extends completely through the second part of connector body 26 from the recess 37 to the passageway 36. Tube 16 is longer than it is shown in FIG. 3; thus being the conduit through which wires or other conductors 17 are passed from the outside and atmospheric venting is carried into the catheter. Those skilled in the art will appreciate that electrical circuitry necessary to provide a pressure probe of the strain gauge type can be connected by means of wires 17 extending through tube 16 from outside the connector body 26 through the opening 19, the passageway 36 and into a lumen 40 of the catheter 13, see FIG. 2.

Figure 4:
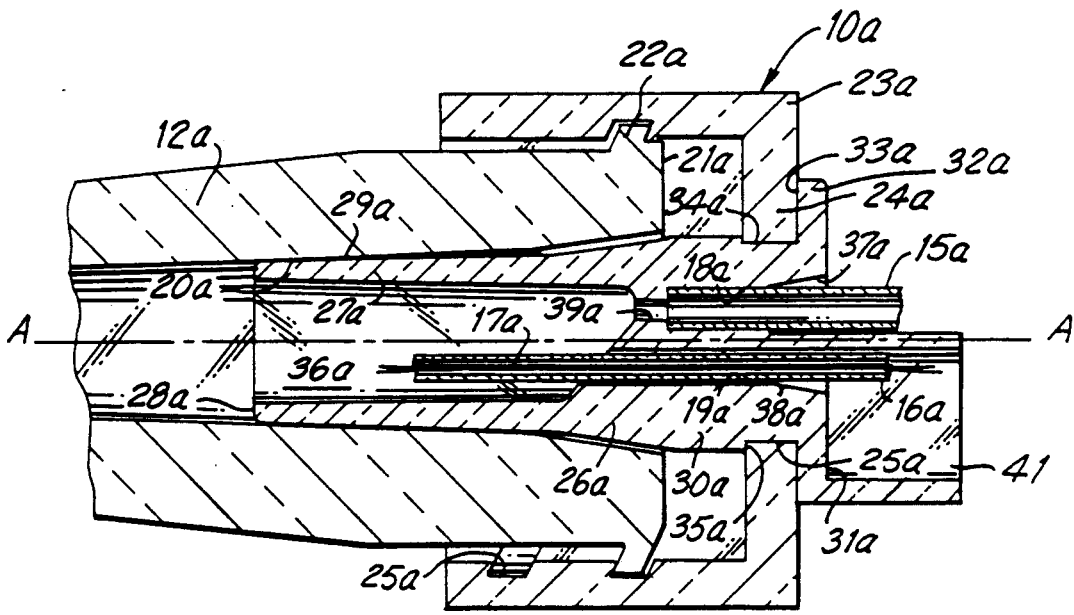
FIG. 4 is an enlarged cross sectional view similar to FIG. 3, of an alternate form of the connector wherein an opening includes a cable coupling extending from the end of the connector.

FIG. 4 is an enlarged cross sectional view, of an alternate form of the connector 10a with a connector body 26a wherein a pair of openings 18a and 19a are provided. Opening 19a includes a coupling 41 extending from a second end 31a of the connector 26a. A catheter or other type of adapter 12a includes on the inside thereof a female luer taper 20a and a radially outward extending flanged end 21a having a luer thread 22a.

A luer nut 23a, shown in FIG. 4, extends over the threaded end of catheter adapter 12a. In particular, luer nut 23a includes an apertured flange end wall 24a the aperture of which is generally coaxial with axis A. Luer nut 23a also includes an internal or female luer thread 25a. The thread 25a is shaped and positioned to cooperate with luer thread 22a on catheter adapter 12a. The apertured flange end wall 24a is of an axial thickness sufficient to provide a bearing-like area of adequate strength and size to permit the luer nut 23a to be supported for rotary but not axial motion relative to the catheter adapter 12a.

The cooperative rotary engagement of the luer nut 23a and the catheter adapter 12a results because connector body 26 includes a first part 27a extending from a first end 28a with a male luer taper 29a designed to cooperate for conjugate interengagement with female luer taper 20a on catheter adapter 12a. That is to say that luer tapers 20a and 29a are such that a fluid tight junction is obtained upon axial movement of one into the other. Connector body 26a also includes a second part 30a extending from a second end 31a having an annular flange 32a with a radial wall 33a against which the luer nut 23a applies axial thrust. Normal to radial wall 33a and upon connector body 26a is a annular groove 34a which circumscribes the connector body 26a in the area of the second part 30a immediately adjacent to radial wall 33a. The annular groove 34a forms a bearing surface for the apertured flange end wall 24a of luer nut 23a. Axially along connector body 26a toward male luer taper 29a but within the annular groove 34a is a shoulder 35a which is part of the annular groove 34a designed to take the axial thrust of the luer nut 23a as it is threaded onto the catheter adapter 12a. The thrust is thereby exerted upon the male luer taper 29a to seat and lock the male luer taper 29a to the female luer taper 20a of the adapter 12a.

Within connector body 26a there is a passageway 36a positioned along axis A and immediately beneath the first part 27a of the connector body 26a which includes the male luer taper 29a. Passageway 36a is in the form of a hollow cavity or bore which extends axially into the connector body 26a from the first end to the point where the male luer taper 29a ends. As part of the second end and extending into the second part 30a of connector body 26a from the annular flange 32a is a recess 37a in the form of a chamfered hole with a bottom 38a through which openings 18a and 19a pass.

Opening 18a has a substantially uniform diameter until a reduced section 39a is reached. Reduced section 39a connects the opening 18a with passageway 36a. Opening 19a has a substantially uniform diameter throughout and extends from the bottom 38a of the recess 37a to the passageway 36a. As shown in FIG. 4 opening 18a has a tube 15a which seats against the reduced section 39a. Opening 19a has a tube 16a which extends completely through the second part of connector body 26a from the coupling 41 in recess 37a to the passageway 36a. Tube 16a is longer than it is shown in FIG. 4; tube 16a is the conduit through which wires or other conductors 17a are passed from the outside into the catheter. Tube 16a is used to provide an atmospheric reference vent for the probe. Coupling 41 provides a place into which a cable sheath (not shown) may be inserted and glued.

Those skilled in the art will appreciate that electrical circuitry necessary to provide a pressure probe of the strain gauge type can be connected by means of wires 17a extending through the cable sheath secure in the coupling 41 and tube 16a from outside the connector body 26a through the opening 19a, the passageway 36a and into a lumen 40a of the catheter 13a. Changes in the materials described, the probe mentioned and the particular configuration of the connector disclosed may be made without departing from the scope of the invention covered by the claims which follow.

What is claimed is:

1. A connector comprising:
 a body with a first end and a second end and a first part on the first end and a second part on the second end, the body having a passageway aligned along an axis of the body and passing through the first part from the first end into the body, the body having a plurality of openings in the second part each of the openings generally parallel to the axis of the body and extending through the second part from the second end to the passageway, the passageway extending from the first end to at least the second part of the body to permit communication through the body from the first end to the second end, the body at the first part being shaped and located for cooperative interengagement with a catheter adapter to permit communication of the passageway with the catheter adapter and a catheter connected thereto; and
 a probe tube with a lumen therethrough, the probe tube passing through at least one of the openings and extending into a portion of the passageway providing the lumen between the first end to the second end.

2. The connector of claim 1 wherein a recess is included as part of the second end for extending into the second part, the recess having a bottom from which the openings pass through the second part to the passageway.

3. The connector of claim 1 wherein the body includes a male luer taper located on the first part of the body about the passageway and tapering outwardly of the axis from the first end to an enlarged diameter for providing a place to connect an adapter.

4. The connector of claim 3 wherein the body includes an annular groove about the body immediately adjacent to the enlarged diameter of male luer taper.

5. The connector of claim 4 wherein a luer nut having an internally threaded collar with an apertured flanged end shaped to seat within the annular groove with the collar extending over the male luer taper, the fit between the groove and collar permitting rotary but not axial movement of the luer nut relative to the connector so as to provide a threaded locking luer.

6. The connector of claim 5 wherein the probe tube lumen contains therein an electrical circuit connecting a catheter transducer attached to the first end to a circuit for receiving input signals from the catheter transducer, the electrical circuitry passing through the probe tube lumen and the passageway.

7. The connector of claim 6 wherein the transducer is a pressure probe.

8. The connector of claim 1 wherein the plurality of openings carry at least an electrical circuit and a tube in substantially parallel spaced apart relation to one another and to the axis.

9. The connector of claim 8 wherein the tube extends from the passageway through the second part and beyond the second end.

10. The connector of claim 1 wherein the first and second ends are substantially parallel to one another.

11. The connector of claim 10 made of a polymeric substance.

12. The connector of claim 11 wherein a polymeric substance is molded to make the body.

13. The connector of claim 2 wherein a coupling in the form of a tubular inlet extends from the bottom of the recess within the body second part providing connection with at least one of the openings.

14. The connector of claim 13 wherein the coupling and the openings are substantially parallel to one another and the axis of the body.

15. A connector comprising:
a body with a first end and a second end and a first part on the first end and a second part on the second end, the body having a passageway aligned along an axis of the body and passing through the first part from the first end into the body, the body at the first part being shaped and located for cooperative interengagement with a catheter adapter to permit communication of the passageway with the catheter adapter and a catheter connected thereto, the body having a plurality of openings in second part each of the openings extending from the second end to at least the passageway in the body to permit communication through the body from the first end to the second end; and
the body having the first and second ends substantially parallel to one another.

16. A connector for an adapter comprising:
a body with a first end and a second end substantially parallel to one another and a first part on the first end and a second part on the second end, the body having a passageway aligned along an axis of the body and passing through the first part from the first end into the body to the second part, the body at the first part being shaped and located for cooperative interengagement with a catheter adapter to permit communication of the passageway with the catheter adapter and a catheter connected thereto, the body having a plurality of openings in the second part each of the openings extending from the second end to at least the passageway in the body to permit communication through the body from the first end to the second end, the openings being in substantially parallel spaced apart relation to one another;
a probe tube with a lumen therethrough, the probe tube passing through at least one of the openings and the passageway, the probe tube being generally parallel to the axis of the body and extending from the first end to the second end;
a recess as part of the second end and in communication with the second part, the recess having a bottom from which the openings pass through the second part to the passageway;
a male luer taper located on the first part of the body about the passageway and tapering outwardly of the axis from the first end to an enlarged diameter for providing a place to connect an adapter;
an annular groove about the body immediately adjacent to the enlarged diameter of the male luer taper;
a luer nut having an internally threaded collar with a flanged portion shaped to fit into the annular groove permitting rotary but not axial movement of the luer nut relative to the body so the collar extends from the second part toward the first end and over the male luer taper providing a threaded locking luer;
a probe tube in one of the openings extending from the passageway through the second part and beyond the second end wherein the openings, the tube and the axis being in substantially parallel spaced apart relation to one another, and
an electrical circuit and atmospheric reference vent in the probe tube passing through the body for the connector for the adapter.

17. A method for providing a plurality of connections between openings and a passageway including the following steps:
providing a body with a first end and a second end and a first part on the first end and a second part on the second end;
locating a passageway along an axis of the body, the passageway passing through the first part from the first end into the body and to the second part;
shaping and locating the body at the first part for cooperative interengagement with a catheter adapter to permit communication of the passageway with the catheter adapter and a catheter connected thereto;
positioning a plurality of openings parallel to one another in the second part;
extending each of the openings from the second end to at least the passageway to permit communication through the body from the first end to the second end, and
providing, parallel to the axis of the body, the passageway and at least one of the openings.

18. The method of claim 17 including the additional step of:
locating a male luer taper on the first part of the body about the passageway;
tapering the male luer outwardly of the axis from the first end to an enlarged diameter, and
providing an annular groove immediately adjacent to the enlarged diameter of male luer taper to connect an adapter.

19. The method of claim 18 with the added step of providing a luer nut with a flanged aperture end to cooperate in a bearing-like relation with the annular groove.

20. The method of claim 19 with the added step of placing the luer nut with a collar having internal threads extending over the male luer taper and an apertured flanged portion shaped to seat within the annular groove permitting rotary but not axial movement of the luer nut relative to the taper so as to provide a threaded locking luer.

21. A connector comprising:
a body with a first end and a second end and a first part on the first end and a second part on the second end, the body having a passageway aligned along an axis of the body and passing through the first part from the first end into the body, the body having a plurality of openings in the second part each of the openings generally parallel to the axis of the body and extending through the second part from the second end to the passageway, the passageway extending from the first end to at least the second part of the body to permit communication through the body from the first end to the second end, the body at the first part being shaped and located for cooperative interengagement with an adapter and wherein a recess is included as part of the second end for extending into the second part, the recess having a bottom from which the openings pass through the second part to the passageway; and
a probe tube with a lumen therethrough, the probe tube passing through at least one of the openings and extending into a portion of the passageway providing the lumen between the first end to the second end.

22. The connector of claim 21 wherein the body includes a male luer taper located on the first part of the body about the passageway and tapering outwardly of the axis from the first end to an enlarged diameter for providing a place to connect an adapter.

23. The connector of claim 22 wherein the body includes an annular groove about the body immediately adjacent to the enlarged diameter of male luer taper.

24. The connector of claim 23 wherein a luer nut having an internally threaded collar with an apertured flanged end shaped to seat within the annular groove with the collar extending over the male luer taper, the fit between the groove and collar permitting rotary but not axial movement of the luer nut relative to the connector so as to provide a threaded locking luer.

25. The connector of claim 24 wherein the probe tube lumen contains therein an electrical circuit connecting a catheter transducer attached to the first end to a circuit for receiving input signals from the catheter transducer, the electrical circuitry passing through the probe tube lumen and the passageway.

26. The connector of claim 25 wherein the transducer is a pressure probe.

27. The connector of claim 21 wherein the plurality of openings carry at least an electrical circuit and a tube in substantially parallel spaced apart relation to one another and to the axis.

28. The connector of claim 27 wherein the tube extends from the passageway through the second part and beyond the second end.

29. The connector of claim 28 wherein the first and second ends are substantially parallel to one another.

30. The connector of claim 29 made of a polymeric substance.

31. The connector of claim 30 wherein a polymeric substance is molded to make the body.

32. The connector of claim 21 wherein a coupling in the form of a tubular inlet extends from the bottom of the recess within the body second part providing connection with at least one of the openings.

33. The connector of claim 32 wherein the coupling and the openings are substantially parallel to one another and the axis of the body.

34. A method for providing a plurality of connections between openings and a passageway including the following steps:
providing a body with a first end and a second end and a first part on the first end and a second part on the second end;
locating a passageway along an axis of the body, the passageway passing through the first part from the first end into the body and to the second part, the body at the first part being shaped and located for cooperative interengagement with an adapter;
positioning a plurality of openings parallel to one another in the second part;
extending each of the openings from the second end to at least the passageway to permit communication through the body from the first end to the second end;
providing, parallel to the axis of the body, the passageway and at least one of the openings;
locating a male luer taper on the first part of the body about the passageway;
tapering the male luer outwardly of the axis from the first end to an enlarged diameter;
providing an annular groove immediately adjacent to the enlarged diameter of male luer taper to connect an adapter;
providing a luer nut with a flanged aperture end to cooperate in a bearing-like relation with the annular groove, and
placing the luer nut with a collar having internal threads extending over the male luer taper and an apertured flanged portion shaped to seat within the annular groove permitting rotary but not axial movement of the luer nut relative to the taper so as to provide a threaded locking luer.

* * * * *